(12) United States Patent
Tegels

(10) Patent No.: US 9,586,033 B2
(45) Date of Patent: Mar. 7, 2017

(54) COLLAPSIBLE SHEATH AND TAPERED DILATOR FOR TISSUE PUNCTURE ACCESS

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 126 days.

(21) Appl. No.: 13/772,933

(22) Filed: Feb. 21, 2013

(65) Prior Publication Data

US 2014/0058429 A1  Feb. 27, 2014

Related U.S. Application Data

(60) Provisional application No. 61/692,980, filed on Aug. 24, 2012.

(51) Int. Cl.
*A61M 29/00* (2006.01)
*A61B 17/34* (2006.01)
*A61B 17/00* (2006.01)

(52) U.S. Cl.
CPC ......... *A61M 29/00* (2013.01); *A61B 17/0057* (2013.01); *A61B 17/3431* (2013.01); *A61B 17/3439* (2013.01); *A61B 17/3417* (2013.01)

(58) Field of Classification Search
CPC ............ A61B 17/0057; A61B 17/3417; A61B 17/3431; A61B 17/3439; A61M 29/00
USPC ... 604/19, 48, 93.01, 96.01, 164.01, 164.03, 604/164.04, 164.1; 606/190–195, 198
See application file for complete search history.

(56) References Cited

U.S. PATENT DOCUMENTS

| | | | |
|---|---|---|---|
| 5,407,430 A * | 4/1995 | Peters | 604/104 |
| 5,814,058 A | 9/1998 | Carlson et al. | |
| 6,626,859 B2 | 9/2003 | von Segesser | |
| 6,692,462 B2 * | 2/2004 | Mackenzie | A61B 17/3415 604/104 |
| 7,618,436 B2 | 11/2009 | Forsberg | |
| 7,618,438 B2 | 11/2009 | White et al. | |
| 7,931,670 B2 | 4/2011 | Fiehler et al. | |
| 2006/0135981 A1 * | 6/2006 | Lenker et al. | 606/191 |
| 2010/0198159 A1 | 8/2010 | Voss et al. | |

OTHER PUBLICATIONS

Notification of Transmittal of the International Search Report and the Written Opinion of the International Searching Authority, or the Declaration for International Application No. PCT/US2013/027064, mailed Jun. 11, 2013 (11 pp.).

* cited by examiner

*Primary Examiner* — Ashley Fishback
(74) *Attorney, Agent, or Firm* — Holland & Hart

(57) ABSTRACT

A tissue puncture access assembly that includes a sheath and a dilator. The sheath is operable between an expanded position with a first maximum outer diameter, and a collapsed position with a second maximum outer diameter that is less than the first maximum outer diameter. The dilator is insertable through the sheath and has a leading end positionable distal of a distal end of the sheath. The sheath is operated into the collapsed position prior to and during insertion with the dilator into a tissue puncture. The sheath is operated into the expanded position once positioned in the tissue puncture.

24 Claims, 10 Drawing Sheets

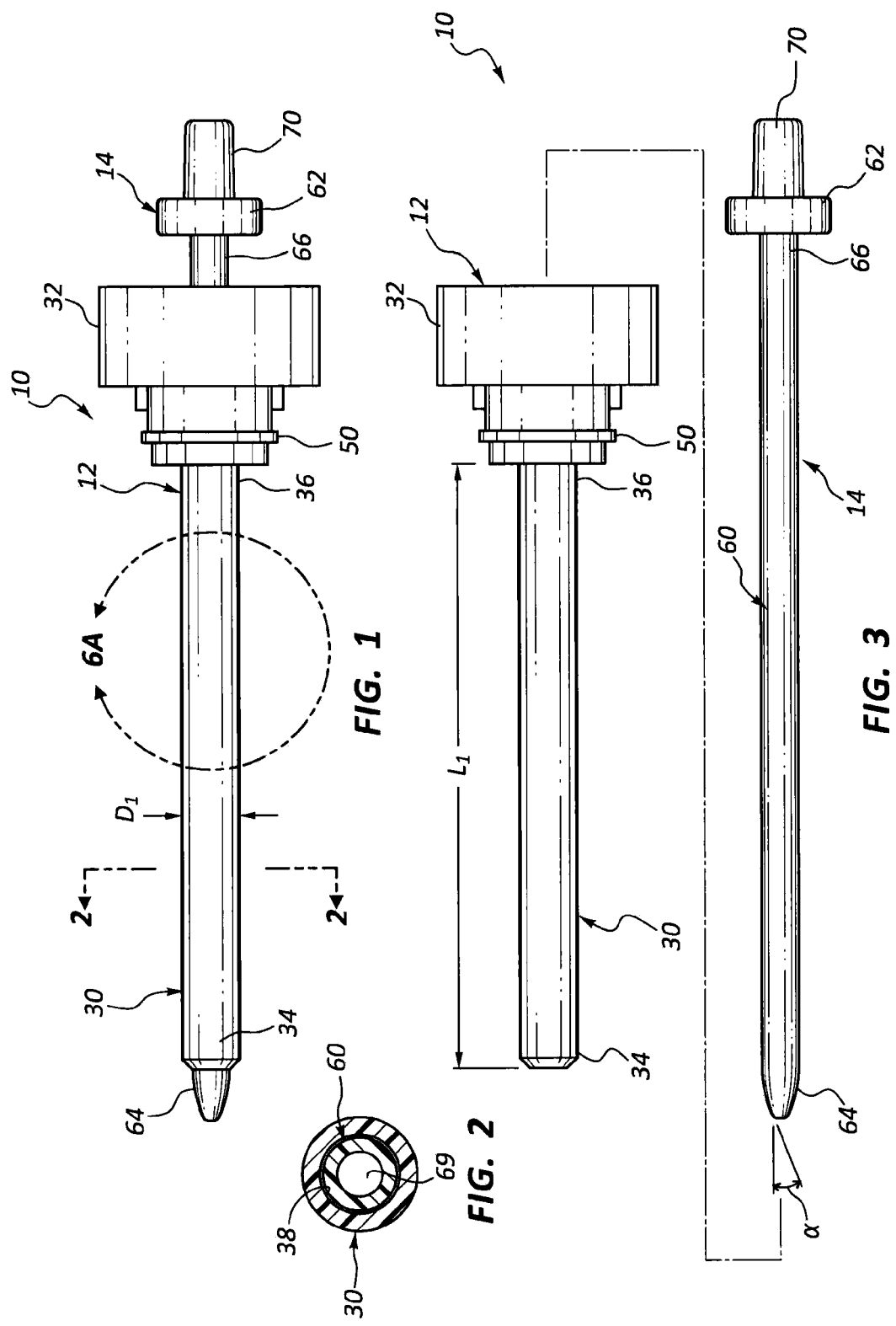

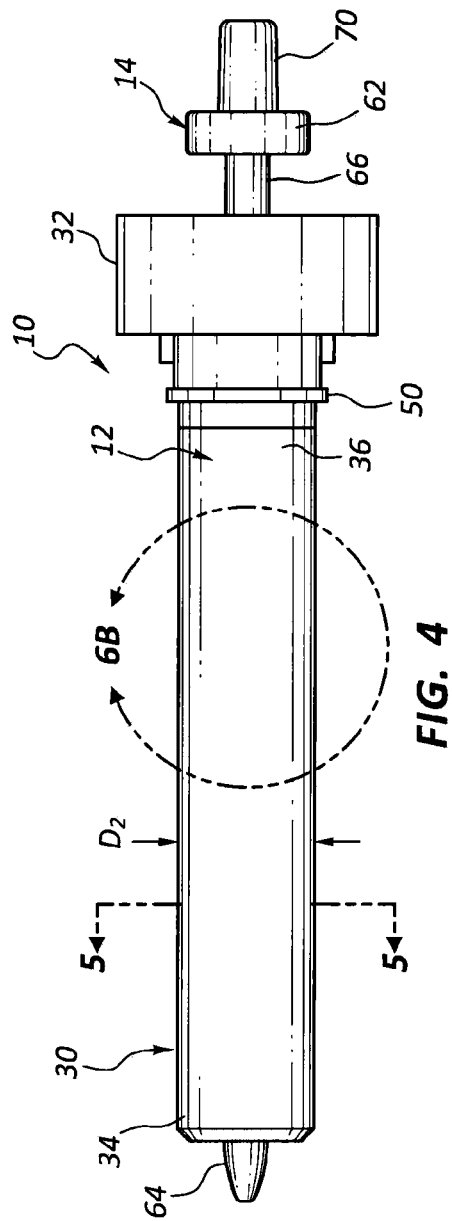
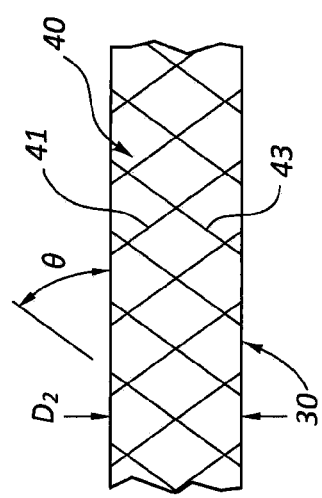
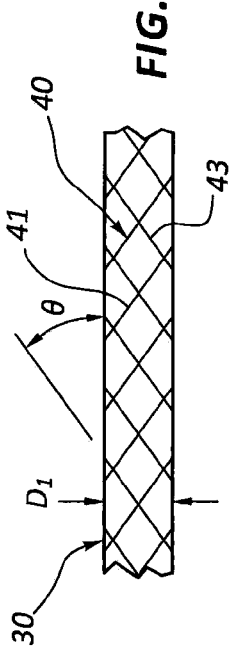
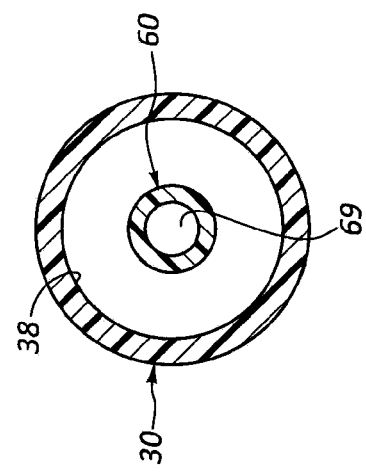

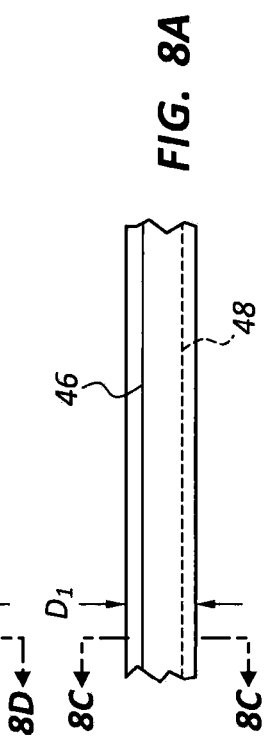
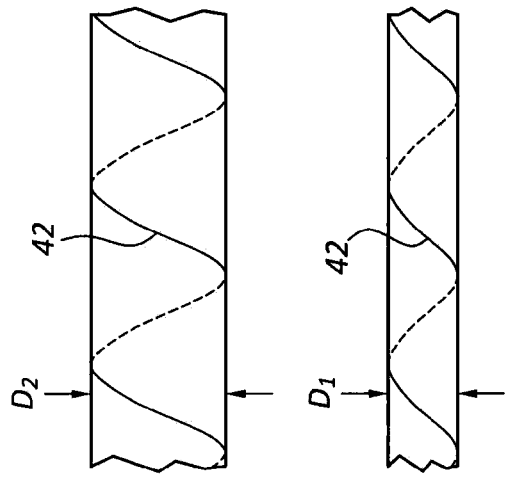
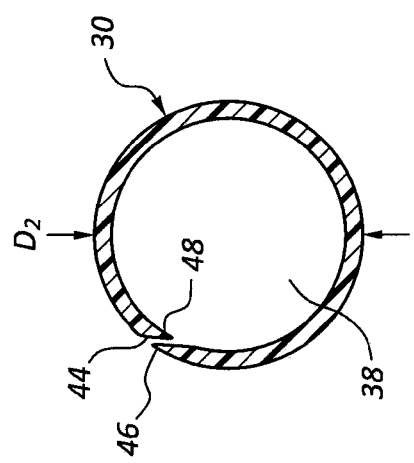
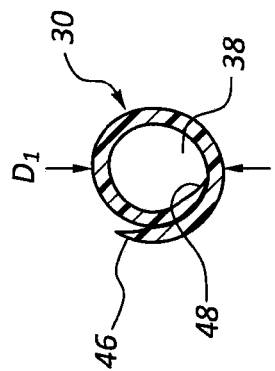

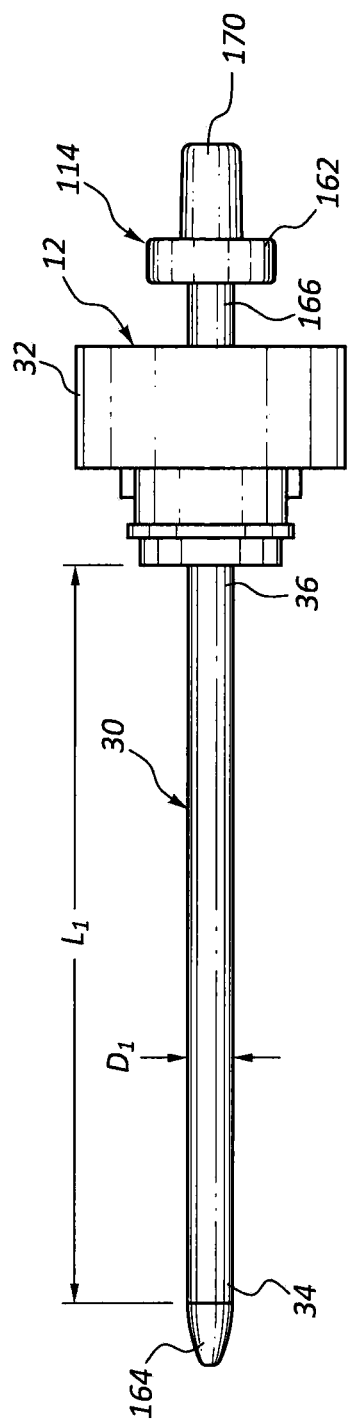
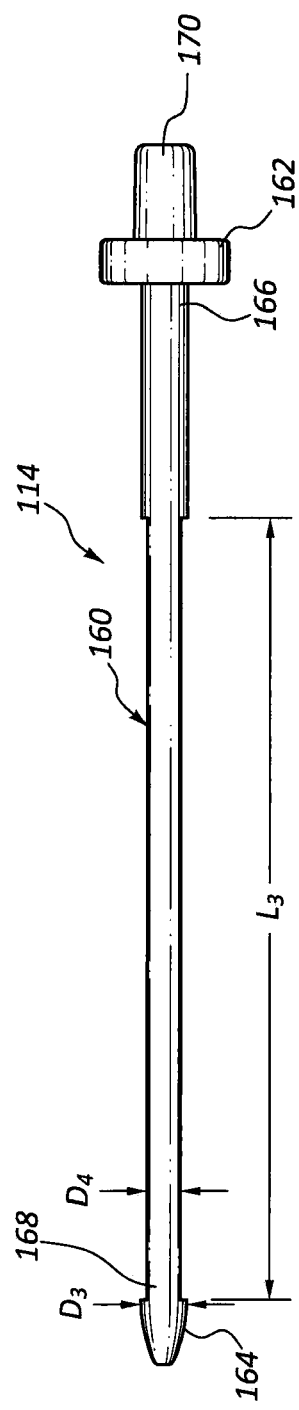
FIG. 9
FIG. 10

COLLAPSIBLE SHEATH AND TAPERED DILATOR FOR TISSUE PUNCTURE ACCESS

RELATED APPLICATION

This claims the benefit of U.S. Provisional Application No. 61/692,980, filed 24 Aug. 2012, which is hereby incorporated by reference herein in its entirety.

TECHNICAL FIELD

The present disclosure relates generally to accessing tissue punctures, and more particularly, to methods and systems for controlling dimensions of a sheath that is insertable through the tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one aspect of interest in the ability to access the puncture prior to closing the puncture. An insertion sheath is commonly inserted into the puncture to create an access port for the closure device used to close the puncture. A dilator is often used with the sheath to dilate or enlarge the puncture at the time of inserting the sheath. The dilator typically extends distal of a distal end of the sheath. The maximum size (e.g., diameter) of the sheath may be greater than the size of the puncture, which presents a challenge to avoid damaging the tissue surrounding the puncture when inserting the sheath.

SUMMARY

One aspect of the present disclosure relates to a tissue puncture access assembly that includes a sheath and a dilator. The sheath is operable between an expanded position with a first maximum outer diameter, and a collapsed position with a second maximum outer diameter that is less than the first maximum outer diameter. The dilator is insertable through the sheath and has a leading end that may be positioned distal of a distal end of the sheath. The sheath may be operable in the collapsed position prior to and during insertion with the dilator into a tissue puncture. The sheath is operated into the expanded position once positioned in the tissue puncture.

The dilator may be operable between an expanded position having a first dilator diameter, and a collapsed position having a second dilator diameter that is less than the first dilator diameter. The sheath may have a first minimum inner diameter in the expanded position, and a second minimum inner diameter in the collapsed position, and the dilator has an outer diameter that is no greater than the first minimum inner diameter of the sheath. The dilator may include a taper at the leading (e.g., distal) end. The leading end of the dilator may taper to a diameter that substantially matches the second maximum outer diameter of the sheath.

The sheath may change shape from the collapsed position to the expanded position in first and second stages, wherein the first stage includes shortening in an axial direction, and the second stage includes expansion in a radial direction. The dilator may include a stepped construction that permits collapsing of the sheath into the collapsed position. The sheath may be operable between the expanded and collapsed positions using a braided construction. The braided construction may be actuated by one of twisting, pushing, pulling or lever action. The sheath may be operable between expanded and collapsed positions using a coil member.

Another aspect of the present disclosure relates to a tissue puncture access assembly that includes a collapsible sheath having a variable outer diameter and a lumen having a variable inner diameter, and a dilator insertable through the lumen of the collapsible sheath. The sheath and dilator are insertable together through a tissue puncture when the sheath is in a collapsed position with a reduced outer diameter. The sheath is also operable into an expanded position with an increased outer diameter when positioned in the tissue puncture to enlarge the tissue puncture.

An outer diameter of the dilator may substantially match the inner diameter of the sheath. The dilator may include a tapered distal end positionable distal of a distal end of the sheath when in the collapsed position. The sheath may be moved between expanded and collapsed positions to change the variable outer diameter using a rotatable collapsing mechanism. The sheath may include a coil member operable to change the sheath between the collapsed position and the expanded position.

A further aspect of the present disclosure relates to a method of accessing a tissue puncture. The method includes providing a collapsible sheath and a dilator, advancing the dilator through the sheath until a distal end of the dilator extends distal of the sheath, operating the sheath into a collapsed position around the dilator, advancing the sheath and dilator through the tissue puncture with the sheath in the collapsed position, and orienting the sheath into an expanded position to dilate the tissue puncture.

Orienting the sheath into the collapsed position may include at least one of reducing an outer diameter of the sheath and increasing a length of the sheath. Orienting the sheath into the collapsed position may include changing a length of the sheath and changing an outer diameter of the sheath. Orienting the sheath into an expanded position may include rotating one end of the sheath relative to an opposite end of the sheath. The method may also include orienting the sheath into the collapsed position around the dilator after dilating the tissue puncture, and withdrawing the sheath and dilator from the tissue puncture.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example sheath assembly in accordance with the present disclosure.

FIG. 2 is a cross-sectional view of the sheath assembly of FIG. 1 taken along cross-section indicators 2-2.

FIG. 3 is an exploded view of the sheath assembly of FIG. 1.

FIG. 4 is a side view showing the sheath assembly of FIG. 1 with the sheath in an expanded position.

FIG. 5 is a cross-sectional view of the sheath assembly of FIG. 4 taken along cross-section indicators 5-5.

FIG. 6A is a close-up view of a portion of the sheath of FIG. 1 having a braid construction.

FIG. 6B is a close-up view of a portion of the sheath of FIG. 4 having a braid construction.

FIG. 7A is a close-up view of a portion of the sheath of FIG. 1 having a coil construction.

FIG. 7B is a close-up view of a portion of the sheath of FIG. 4 having a coil construction.

FIG. 8A is a close-up view of a portion of the sheath of FIG. 1 having a collapsible slit construction.

FIG. 8B is a close-up view of a portion of the sheath of FIG. 4 having a collapsible slit construction.

FIG. 8C is a cross-sectional view of the portion of the sheath of FIG. 8A.

FIG. 8D is a cross-sectional view of the portion of the sheath of FIG. 8B.

FIG. 9 shows another example sheath assembly in accordance with the present disclosure.

FIG. 10 shows the dilator of the sheath assembly of FIG. 9 having a step construction.

Throughout the drawings, identical reference numbers designate similar, but not necessarily identical, elements.

DETAILED DESCRIPTION

Figure 11:
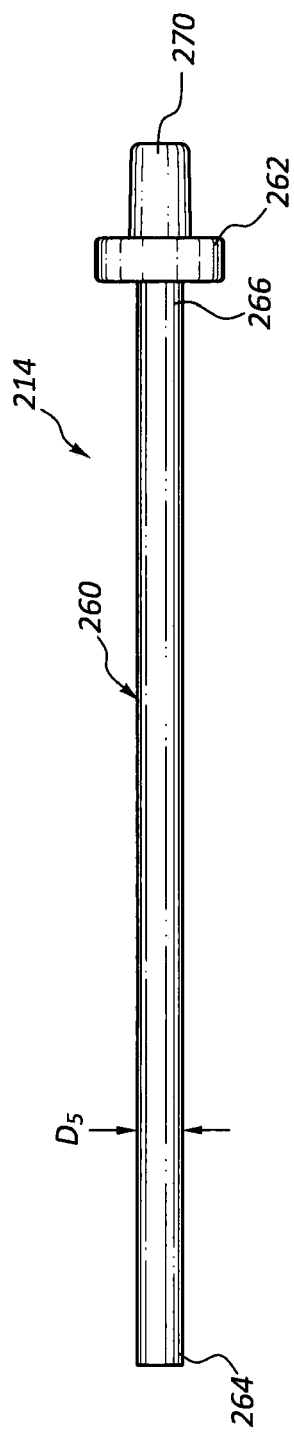
FIG. 11 shows another example dilator in accordance with the present disclosure.

The apparatuses and methods disclosed herein may be used to access percutaneous punctures made through a body layer of a patient to gain access to a body cavity. Access through a percutaneous puncture allows a physician to carry out various procedures in or through the body cavity for examination, surgery, treatment and the like. While not meant to be limiting, the systems are illustrated being used to access percutaneous punctures in blood vessels in patients for various procedures. It will be appreciated that the apparatuses and methods are applicable to other procedures requiring access to a puncture through body tissue into a cavity including, for example, laparoscopic surgery and other microscopic surgery techniques using a relatively small incision. Applications of access apparatuses and methods including those implementing principles described herein include access of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

One aspect of the present disclosure is directed to a sheath assembly that includes a sheath and a dilator. At least one of the sheath and dilator are configured to operate between expanded and collapsed shapes or positions. In one example, the sheath may be operated between a collapsed position having a reduced outer profile (e.g., outer diameter) that facilitates easier insertion into a tissue puncture, and an expanded position that assists in dilating or expanding the tissue puncture after positioning the sheath within the tissue puncture. The sheath assembly may be particularly useful when attempting to increase the tissue puncture size from, for example, about 3 to 6 French to an expanded size of about 10 to 20 French. Attempting to insert or remove a relatively large diameter sheath (e.g., in the size of about 10 to 20 French) relative to a smaller sized tissue puncture may create undesired damage to the tissue.

The sheath assembly of the present disclosure may provide for a reduced profile sheath when asserting the sheath assembly through the tissue puncture, and provide later expanding of the sheath to dilate the tissue puncture after the sheath assembly is properly positioned within the tissue puncture. The sheath assembly may also be collapsible after conducting a treatment procedure via access provided by the sheath. Collapsing the sheath prior to removing the sheath assembly may also help limit damage to the tissue that defines the tissue puncture.

An example dilator of the sheath assembly may have a tapered distal end portion to help transition from a smaller diameter distal tip of the dilator to a larger diameter distal end of the sheath. The dilator may include a step feature that provides a reduced diameter outer surface along a portion of a length of the dilator proximal of the distal end of the dilator. The step feature may accommodate a portion of the sheath, which when collapsed may have an outer diameter that is similar in size to a maximum diameter of the distal end portion of the dilator. The step feature in the dilator may provide an improved shape transition from the distal tip of the dilator to the sheath.

Various mechanical constructions and devices may be implemented to operate the sheath between expanded and collapsed positions. One example mechanism includes a tubular braided structure. Applying an axially directed force to the braided structure may change an outer diameter of the sheath. In another example, the sheath includes a coil structure along at least a portion of its length. Rotating the coil structure may change an outer diameter of the sheath. Operating the braid and coil structures may also change a length of the sheath. In a still further example, the sheath includes a longitudinal slit, wherein the longitudinal slit defines opposing side edges that are moveable circumferentially and/or radially relative to each other. In a collapsed position, the slit side edges overlap each other to provide a reduced outer dimension for the sheath. In an expanded position, the slit side edges are arranged adjacent to each other to provide an increased outer diameter for the sheath. The relative movement between the slit side edges may be implemented by applying, for example, a rotation force to one end of the sheath.

In a still further example, the dilator may also be operated between expanded and collapsed positions. The outer diameter of the dilator may change to more closely match an inner diameter of the sheath as the sheath is operated between expanded and collapsed positions. In at least one example, operating the dilator between expanded and collapsed positions assists in changing the sheath between expanded and collapsed positions. The dilator may be used to advance the sheath assembly through a tissue puncture and then be removed from the sheath prior to conducting treatment of the patient with instruments that extend through the sheath 12. Typically, the sheath is collapsed prior to removing the sheath from the tissue puncture.

Referring now to FIGS. 1-5, an example sheath assembly 10 is shown and described. The sheath assembly 10 includes a sheath 12 and a dilator 14. The dilator 14 extends through the sheath 12 such that a distal end of the dilator extends distally of a distal end of the sheath. A proximal end of the dilator is positioned proximal to the proximal end of the sheath so that the operator can operate and move the dilator 14 relative to the sheath 12. In some arrangements, the sheath is operated into an at least partially expanded position prior to inserting the dilator 14 through the sheath 12. In other arrangements, the dilator 14 may be advanced through the sheath 12 when the sheath is in a substantially collapsed position.

The sheath 12 includes a sheath body 30 and a hub 32. The sheath body 30 includes distal and proximal ends 34, 36, a lumen 38 (see FIGS. 2 and 5), a collapsed outer diameter $D_1$ (see FIG. 1), and an expanded outer diameter $D_2$ (see FIG. 4). The sheath body 30 may also include a collapsed length $L_1$ (see FIG. 3) and an expanded length (not shown).

The hub 32 is connected to the proximal end 36 of the sheath body 30. The hub 32 may include an actuator 50, which when operated changes the sheath body from the collapsed position shown in FIG. 1 to the expanded position shown in FIG. 4. Operating (e.g., orienting) the actuator 50 may also change the sheath body 30 from the expanded position shown in FIG. 4 to the collapsed position shown in FIG. 1.

The actuator 50 is shown schematically in the figures and may represent any desired actuation device. In one example, the actuator 50 may be rotatable about a longitudinal axis of the sheath 12 to change the sheath body 30 between collapsed and expanded positions. In other arrangements, the actuator 50 may move axially to operate the sheath body 30 between collapsed and expanded positions. In still further arrangements, the actuator 50 may include, for example, fasteners, clips, gauges, indicia, threads, pull wires, or other features that may be used to operate the sheath body between collapsed and expanded positions and help maintain the sheath body in collapsed and expanded positions. The actuator 50 may be directly connected to the sheath body 30. In other arrangements, the actuator 50 may include an intervening member that couples the actuator 50 to the sheath body 30 or a portion of the sheath body used to operate the sheath body 30 between collapsed and expanded positions.

In at least some arrangements, operating or orienting the sheath body 30 between expanded and collapsed positions changes both the outer diameter as well as the length of the sheath body 30. For example, the sheath body 30 may have an outer diameter $D_1$ and a length $L_1$ when in a collapsed position. Operating the sheath body 30 into an expanded position changes the outer diameter to an enlarged outer diameter $D_2$ and changes the length to a shortened, expanded length $L_2$ (see FIG. 4). In some arrangements, increasing the outer diameter automatically shortens the length of the sheath body 30, and decreasing the outer diameter automatically increases the length of the sheath body 30. In other arrangements, increasing the length of the sheath body 30 automatically decreases the outer diameter, and decreasing the length of the sheath body 30 automatically increases the outer diameter.

Referring to FIGS. 6A and 6B, an example construction for the sheath body 30 includes a braid 40. In the collapsed position of FIG. 6A, at least some of structures 41, 43 of braid 40 may be arranged at an angle θ in the range of about 20° to about 45°. In the expanded position of FIG. 6B, the structures 41, 43 of braid 40 may be arranged at an angle θ of about 45° to about 90°. The structures 41, 43 may extend in generally opposite directions. The braid 40 may be operated by, for example, applying a rotation force to one end of the sheath body 30 while maintaining an opposite end of the sheath body in a generally fixed rotated position. In another arrangement, the braid structure is operated by rotating the opposing ends in opposite directions. Alternately, the braid structure may be operated by applying a longitudinal force to the sheath body 30.

Referring now to FIGS. 7A and 7B, the sheath body 30 is shown including a coil structure 42. The coil structure 42 may be operated to move the sheath body between collapsed and expanded positions by either rotating or applying a longitudinal force to one end of the coil structure 42. The sheath body 30 may include multiple coil members. The coil members may be arranged co-extensive, or may be arranged radially inward from each other. Many arrangements are possible for coil structures in a sheath body 30.

Referring to FIGS. 8A-D, the sheath body 30 is shown including a longitudinal slit 44 having first and second longitudinal slit edges 46, 48. In the collapsed position, the first and second longitudinal edges 46, 48 are positioned overlapping each other (see FIG. 8C). In the expanded position, the first and second longitudinal edges 46, 48 may be positioned adjacent to each other and possibly arranged facing each other as shown in FIG. 8D. The longitudinal slit 44 may be arranged linearly along a length of the sheath body 30. Alternatively, longitudinal slit 44 may be arranged in a helical path along the length of the sheath body 30. The sheath body 30 including the longitudinal slit 44 may be operated between collapsed and expanded positions, for example, by applying longitudinal or rotational forces to one end of the sheath body 30.

In another example (not shown), the sheath 12 may include a pull wire or other device that extends along at least a portion of the length of the sheath body 30. Operating the pull wire may apply an axially directed force to the sheath body 30 that changes the outer diameter between the collapsed outer diameter $D_1$ and the expanded outer diameter $D_2$.

Referring now to FIGS. 1 and 3, the dilator 14 includes a body portion 60 and a hub 62. The body portion 60 includes distal and proximal end portions 64, 66, a lumen 69 (see FIG. 2), and an outer diameter $D_3$. The distal end portion 64 of the body portion 60 may include a taper having a taper angle α (see FIG. 3). The tapered construction of the distal end portion 64 may improve insertability of the sheath assembly 10 through a relatively small tissue puncture. The tapered construction of the distal end portion 64 may transition to a larger outer diameter $D_3$ of the body portion 60 and the collapsed outer diameter $D_1$ of the sheath body 30.

In operation, the dilator 14 is inserted through the hub 32 of the sheath 12 and into the sheath body 30 until the distal end portion 64 extends distal of the distal end 34 of the sheath body 30. In at least some arrangements, the diameter $D_3$ is less than the diameter $D_1$ of the sheath body 30. A more smooth transition from the distal end portion 64 of the body portion 60 to the sheath body 30 may be possible by providing a step feature along a portion of the length of the dilator 14 that overlaps with the sheath body 30. FIGS. 9 and 10 show an alternative dilator 114 construction that includes a step feature. The dilator 114 includes a body portion 160 and a hub 162 that includes an actuator portion 170 used to move the dilator 114 relative to the sheath 12.

The body portion 160 includes distal and proximal ends 164, 166 and a step 168 having a reduced diameter $D_4$. The step 168 has a step length $L_3$ that is at least as long as the collapsed and expanded lengths $L_1$, $L_2$ of the sheath body 30. The reduced diameter $D_4$ of the step 168 provides a space along the dilator 114 for the sheath body 30 to collapse into. The sheath body 30 may have a smaller collapsed outer diameter $D_1$ as compared to the collapsed outer diameter $D_1$ possible with the sheath assembly 10 shown in FIGS. 1-5. The diameter $D_3$ at the distal end 164 of the body portion 160 may be substantially the same as the collapsed outer diameter $D_1$ of the sheath body 30 as shown in FIG. 9.

Figure 12:
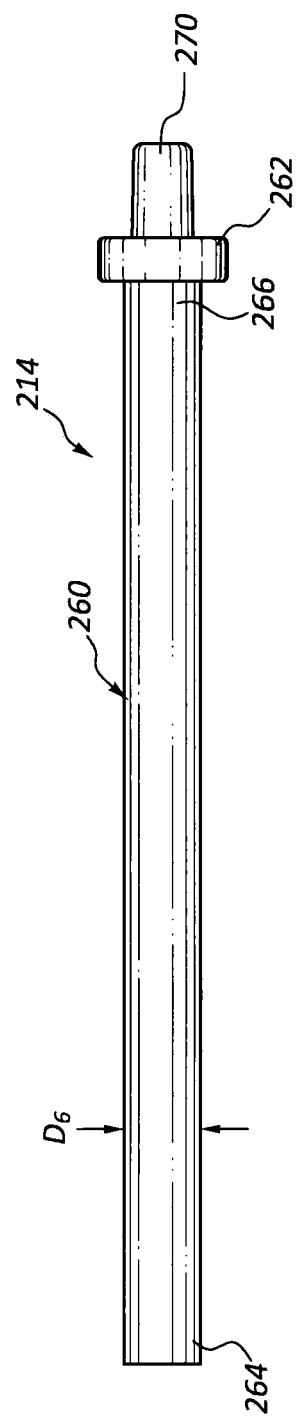
FIG. 12 shows the dilator of FIG. 11 in an expanded position.

Referring now to FIGS. 11 and 12, another example dilator 214 is shown and described. The dilator 214 may include a body portion 260 and a hub 262. The body portion 260 may include distal and proximal ends 264, 266. The hub 262 may include an actuator 270. The body portion 260 may be operable between collapsed and expanded positions. The body portion 260 may have a constant diameter along its entire length rather than including a tapered structure at a distal end (e.g., see body portions 60, 160). The body portion may have a collapsed outer diameter $D_5$ when in a collapsed position (see FIG. 11), and an expanded outer diameter $D_6$ when in an expanded position (see FIG. 12).

The dilator 214 may be used to help expand and collapse the sheath 12. In some arrangements, the dilator 214 is expanded and collapsed concurrently with expanding and collapsing the sheath 12. In some arrangements, the dilator 214 may be expanded only after completion of expansion of the sheath 12 and must be collapsed prior to collapsing the sheath 12. In the expanded position of FIG. 12, the dilator 214 may have an expanded outer diameter $D_6$ that substantially matches an inner diameter of the sheath 12 in the expanded position of FIG. 4.

The actuator 270 may be used to operate the dilator 214 between the collapsed and expanded positions shown in FIGS. 11 and 12. The actuator 270 may, for example, apply a rotational force or an axial force to the body portion 260 that provides expanding and collapsing. The body portion 260 may have any one of the constructions described above for the sheath 12 with reference to FIGS. 6A-8D. The actuator features and construction for the body portion 260 of the dilator 214 may be similar to what is included in the sheath 12 (e.g., a braid, coil, or longitudinal slit).

Those features of the sheath assemblies disclosed herein that provide collapsing and expansion of at least one of the sheath and dilator may include a shape memory material such as Nitinol. Other materials or objects that may be useful include, for example, coil springs.

Figure 13:
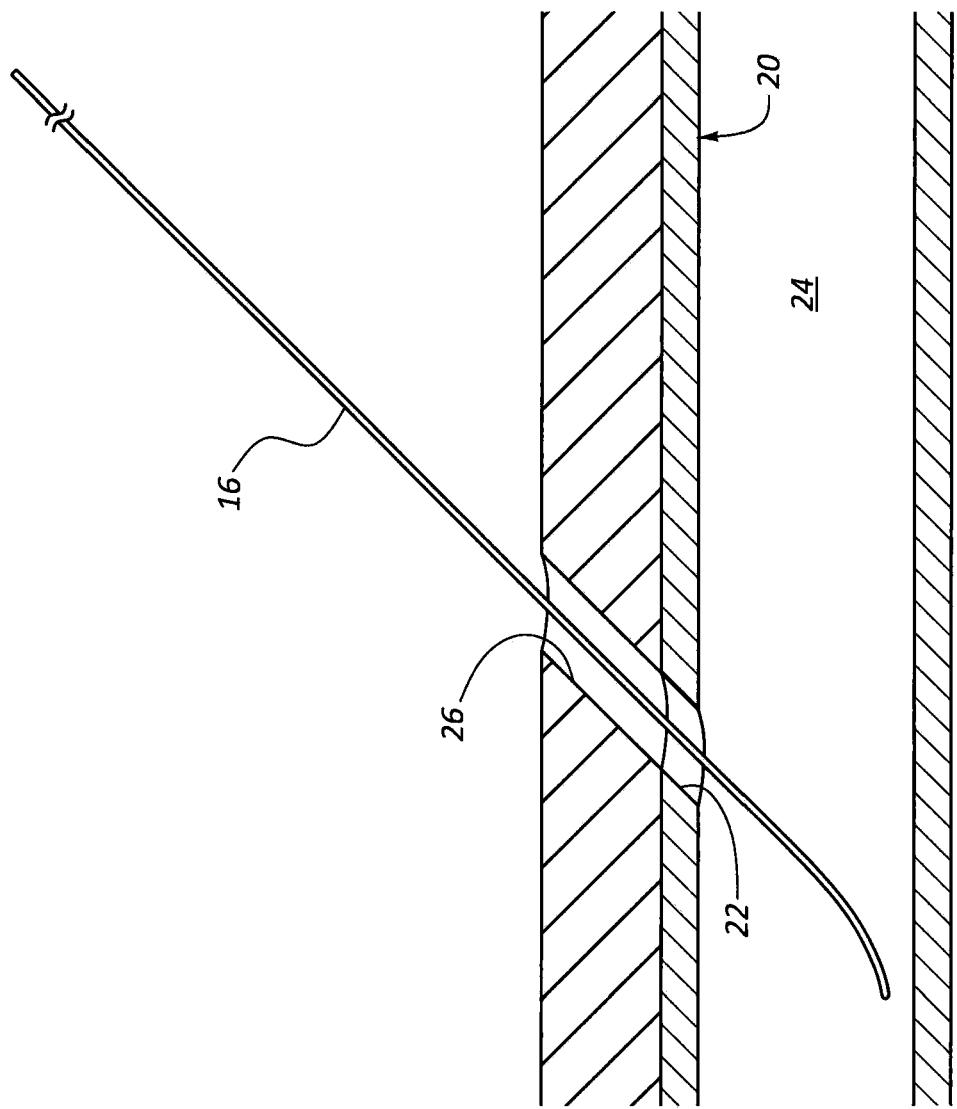
FIGS. 13-17 show steps of expanding a tissue puncture using the sheath assembly of FIG. 1.
Figure 14:
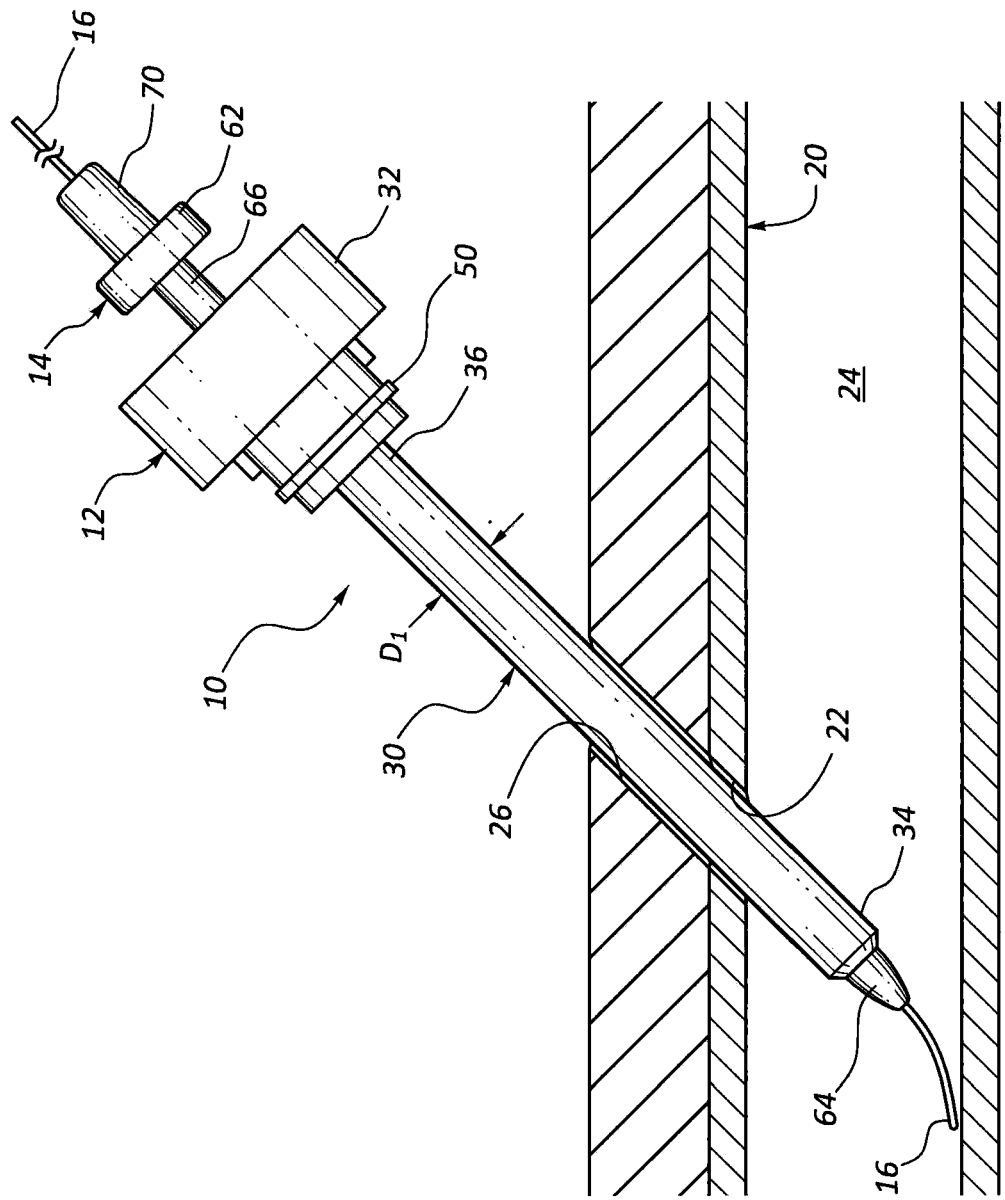

Referring now to FIGS. 13-17, an example method of operating the sheath assembly 10 is shown and described. Typically, a first step in operating the sheath assembly 10 to expand a tissue puncture and provide access to a body cavity (e.g., a vessel lumen) includes positioning a guidewire 16 extending through the tissue puncture. In the example of FIGS. 13-17, the tissue puncture includes a percutaneous incision 26 and vessel puncture 22 that provide access to a vessel lumen 24 of a vessel 20. With the guidewire 16 properly positioned as shown in FIG. 13, the sheath assembly 10 is advanced along the guidewire 16 and into the vessel lumen 24. Prior to advancing the sheath assembly 10 along the guidewire 16, the sheath 12 is operated into a collapsed position having a collapsed outer diameter $D_1$. The dilator 14 may include a tapered distal end portion 64 that assists in advancing the sheath assembly 10 through the percutaneous incision 26 and vessel puncture 22, which have a reduced original size. This initial advancing of the sheath assembly 10 along the guidewire 16 into the vessel lumen 24 may provide some preliminary dilation or expansion of the percutaneous incision 26 and vessel puncture 22.

Figure 15:
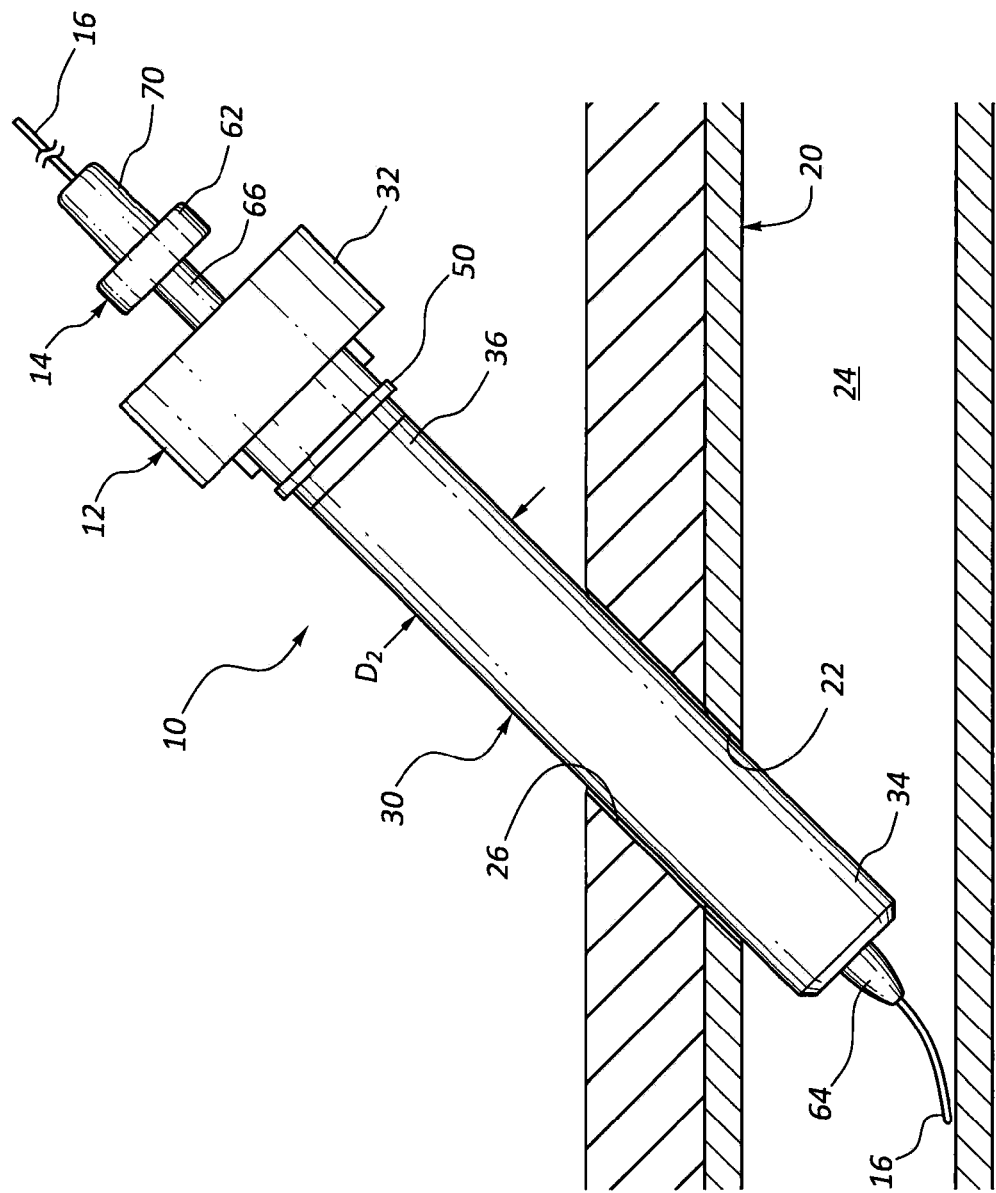
Figure 16:
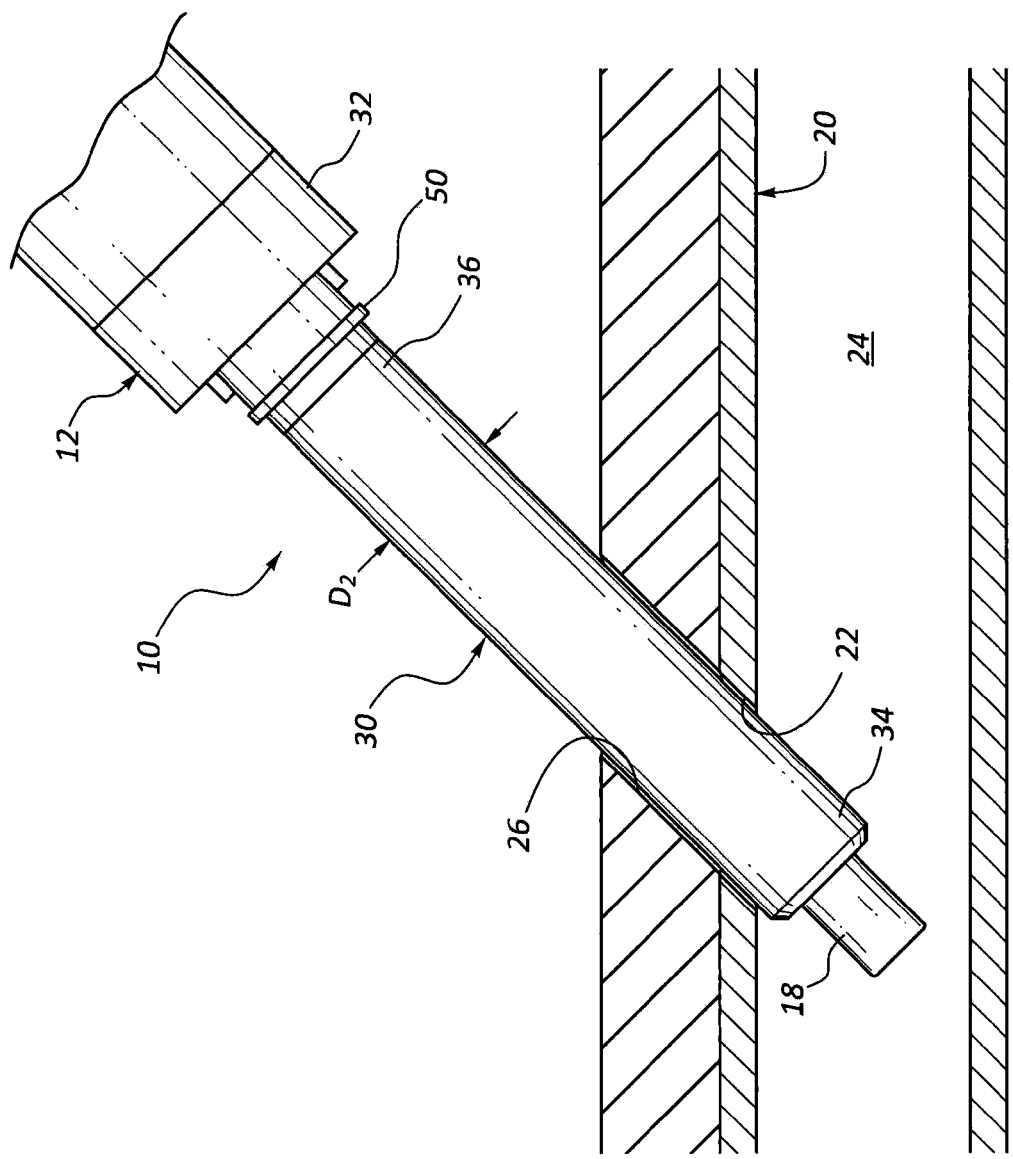

Referring to FIG. 15, the sheath 12 is operated into an expanded position having an expanded outer diameter $D_2$. The sheath 12 may be operated into the expanded position by operating the actuator 50. The expanded outer diameter $D_2$ enlarges the percutaneous incision 26 and vessel puncture 22. Thereafter, the dilator 14 and guidewire 16 are removed from the sheath 12. A treatment device 18 may be advanced through the sheath 12 and into the vessel lumen 24 as shown in FIG. 16. The treatment device 18 may be operated to treat the patient. After the treatment is completed, the treatment device 18 is removed from the sheath 12.

Figure 17:
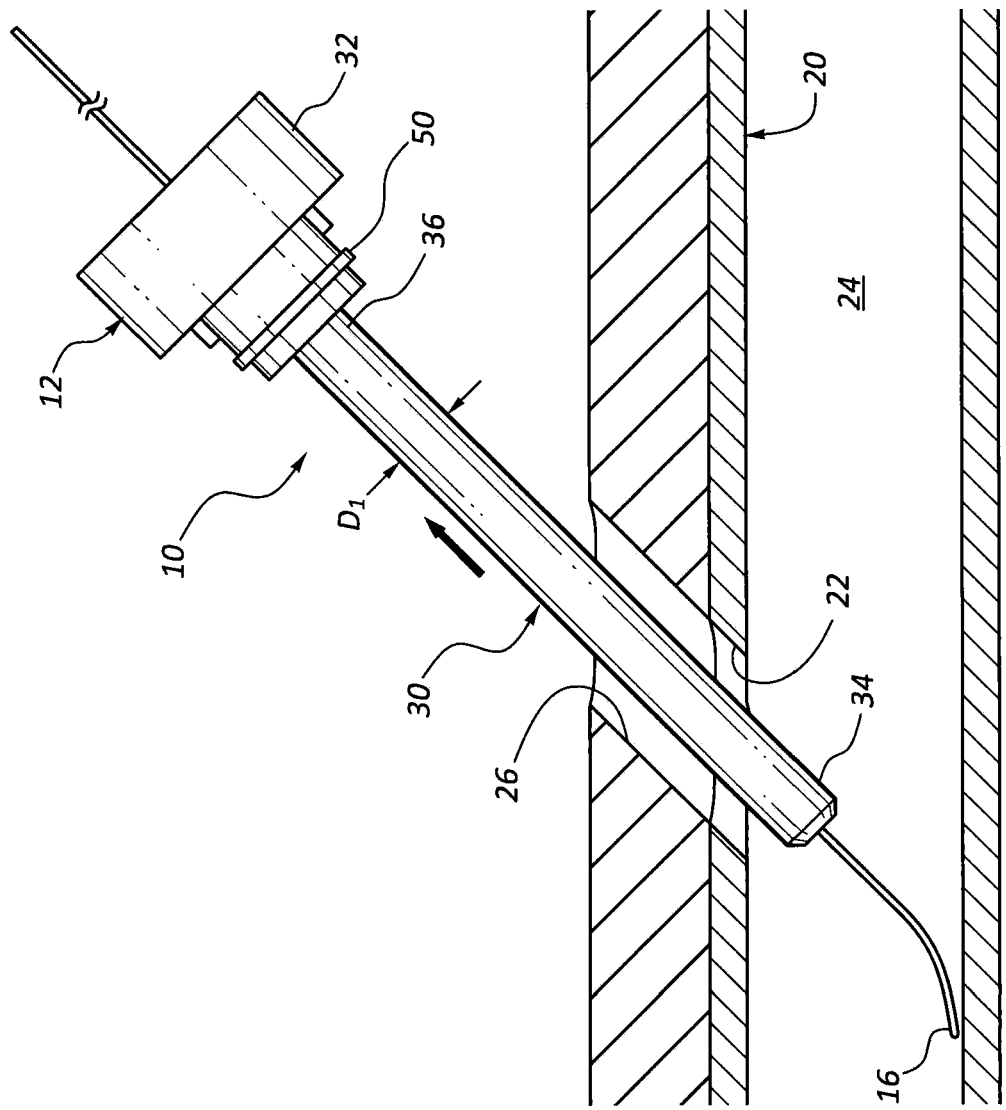

The sheath 12 may be operated from the expanded position shown in FIG. 16 to the collapsed position shown in FIG. 17. The collapsed position after treatment is completed may include a shape for the sheath 12 that is similar to the collapsed position provided at the time of advancing the sheath assembly 10 over the guidewire 16 described with reference to FIG. 14. Prior to removing the sheath 12 from the percutaneous incision 26 and vessel puncture 22, the guidewire 16 may be reinserted into the vessel lumen 24 to maintain access into the vessel lumen 24. Collapsing the sheath 12 to the collapsed outer diameter $D_1$ prior to removal may help limit tissue damage in and around the percutaneous incision 26 and vessel puncture 22.

In some arrangements, the sheath 12 may be used as part of a vessel closure procedure to seal closed the percutaneous incision 26 and vessel puncture 22. Many example closure devices may be used with the sheath 12 including, for example, the devices disclosed in U.S. Pat. Nos. 7,931,670, 7,618,438 and 7,618,436, which are incorporated herein in their entireties by this reference.

In some arrangements, the sheaths of the sheath assemblies disclosed herein are operable independent of the dilator. The sheath may include a tapered distal end that provides at least some of the benefits of using a dilator. The sheath may be inserted through a tissue puncture while in a collapsed position, operated into an expanded position to expand the tissue puncture and provide a path for treatment instruments into the patient, and then operated into a collapsed position prior to being removed from the tissue puncture. The dilators disclosed herein may also be used independent of a collapsible sheath or may be used with various sheaths having different features and functionality as compared to a collapsible sheath.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture access assembly, comprising:
a sheath having an expanded position with a first maximum outer diameter, and a collapsed position with a second maximum outer diameter that is less than the first maximum outer diameter;
a dilator extending through the sheath, the dilator having a leading end having an outer diameter positioned distal of a distal end of the sheath, the dilator having a step portion surrounded by the sheath, the step portion having a reduced outer diameter relative to the outer diameter of the leading end of the dilator, the dilator comprising a proximal end, the proximal end comprising a hub;
wherein the sheath is operable between a collapsed position and an expanded position while the leading end of the dilator is positioned distal of the distal end of the sheath;
wherein the second maximum outer diameter of the sheath is equal to the outer diameter of the leading end of the dilator.

2. The tissue puncture access assembly of claim 1, wherein the sheath has a first minimum inner diameter in the expanded position, and a second minimum inner diameter in the collapsed position, and the dilator has an outer diameter that is no greater than the first minimum inner diameter of the sheath.

3. The tissue puncture access assembly of claim 1, wherein the dilator includes a taper at the leading end.

4. The tissue puncture access assembly of claim 1, wherein the outer diameter of the leading end of the dilator tapers to the second maximum outer diameter.

5. The tissue puncture access assembly of claim 1, wherein the sheath changes shape from the collapsed position to the expanded position in first and second stages, the first stage including shortening in an axial direction, and the second stage including expansion in a radial direction.

6. The tissue puncture access assembly of claim 1, wherein the dilator includes a stepped construction that permits collapsing of the sheath into the collapsed position.

7. The tissue puncture access assembly of claim 1, wherein the sheath is operable between the expanded and collapsed positions using a braided construction.

8. The tissue puncture access assembly of claim 7, wherein the braided construction is actuated by one of twisting, pushing, pulling or lever action.

9. The tissue puncture access assembly of claim 1, wherein the sheath is operable between expanded and collapsed positions using a coil member.

10. A tissue puncture access assembly, comprising:
a collapsible sheath having a distal end, a variable outer diameter, and a lumen having a variable inner diameter;
a dilator inserted through the lumen of the collapsible sheath, the dilator having a proximal end, the dilator having a distal end positioned distal of the distal end of the collapsible sheath, the distal end of the dilator having an outer diameter, the dilator having a reduced diameter portion, the reduced diameter portion having a diameter that is less than the outer diameter of the distal end of the dilator, the proximal end of the dilator being integrated with a hub;
wherein the collapsible sheath is operable between a collapsed position with a reduced outer diameter and an expanded position with an increased outer diameter while the distal end of the dilator is positioned distal of the distal end of the collapsible sheath.

11. The tissue puncture access assembly of claim 10, wherein an outer diameter of the dilator matches the variable inner diameter of the collapsible sheath.

12. The tissue puncture access assembly of claim 10, wherein the dilator includes a tapered distal end positionable distal of a distal end of the collapsible sheath when in the collapsed position.

13. The tissue puncture access assembly of claim 10, wherein the collapsible sheath is moved between expanded and collapsed positions to change the variable outer diameter using a rotatable collapsing mechanism.

14. The tissue puncture access assembly of claim 10, wherein the collapsible sheath includes a coil member operable to change the collapsible sheath between the collapsed position and the expanded position.

15. The tissue puncture access assembly of claim 10, wherein at least part of the dilator has a dilator outer diameter that is greater than the variable inner diameter of the collapsible sheath while the collapsible sheath is in the collapsed position.

16. A method of accessing a tissue puncture, comprising:
providing a collapsible sheath and a dilator, the dilator having a proximal end, the proximal end comprising a hub, the hub being movable relative to the collapsible sheath;
advancing the dilator through the collapsible sheath until a distal end of the dilator extends distal of the collapsible sheath and a length of the collapsible sheath surrounds a portion of the dilator having a reduced diameter relative to the distal end of the dilator;
orienting the collapsible sheath into a collapsed position around the dilator, wherein the distal end of the dilator has an outer dilator diameter equal to an outer collapsible sheath diameter in the collapsed position;
advancing the collapsible sheath and dilator through the tissue puncture with the collapsible sheath in the collapsed position;
orienting the collapsible sheath into an expanded position to dilate the tissue puncture.

17. The method of claim 16, wherein orienting the collapsible sheath into the collapsed position includes at least one of reducing an outer diameter of the collapsible sheath and increasing a length of the collapsible sheath.

18. The method of claim 16, wherein orienting the collapsible sheath into the collapsed position includes changing a length of the collapsible sheath and changing an outer diameter of the collapsible sheath.

19. The method of claim 16, wherein orienting the collapsible sheath into an expanded position includes rotating one end of the collapsible sheath relative to an opposite end of the collapsible sheath.

20. The method of claim 16, further comprising orienting the collapsible sheath into the collapsed position around the dilator after dilating the tissue puncture, and withdrawing the collapsible sheath and dilator from the tissue puncture.

21. A tissue puncture access assembly, comprising:
a sheath having an expanded position with a first maximum outer diameter, and a collapsed position with a second maximum outer diameter that is less than the first maximum outer diameter;
a dilator extending through the sheath, the dilator having a leading end having an outer diameter positioned distal of a distal end of the sheath, the dilator having a step portion surrounded by the sheath, the step portion having a reduced outer diameter relative to the outer diameter of the leading end of the dilator;

wherein the sheath is operable between a collapsed position and an expanded position while the leading end of the dilator is positioned distal of the distal end of the sheath;

wherein the second maximum outer diameter of the sheath is equal to the outer diameter of the leading end of the dilator, and wherein the sheath is operable between expanded and collapsed positions using a coil member.

22. A tissue puncture access assembly, comprising:
a collapsible sheath having a distal end, a variable outer diameter, and a lumen having a variable inner diameter;
a dilator inserted through the lumen of the collapsible sheath, the dilator having a distal end positioned distal of the distal end of the collapsible sheath, the distal end of the dilator having an outer diameter, the dilator having a reduced diameter portion, the reduced diameter portion having a diameter that is less than the outer diameter of the distal end of the dilator;
wherein the collapsible sheath is operable between a collapsed position with a reduced outer diameter and an expanded position with an increased outer diameter while the distal end of the dilator is positioned distal of the distal end of the collapsible sheath, and wherein the collapsible sheath is moved between expanded and collapsed positions to change the variable outer diameter using a rotatable collapsing mechanism.

23. A tissue puncture access assembly, comprising:
a collapsible sheath having a distal end, a variable outer diameter, and a lumen having a variable inner diameter;
a dilator inserted through the lumen of the collapsible sheath, the dilator having a distal end positioned distal of the distal end of the collapsible sheath, the distal end of the dilator having an outer diameter, the dilator having a reduced diameter portion, the reduced diameter portion having a diameter that is less than the outer diameter of the distal end of the dilator;
wherein the collapsible sheath is operable between a collapsed position with a reduced outer diameter and an expanded position with an increased outer diameter while the distal end of the dilator is positioned distal of the distal end of the collapsible sheath, and wherein the collapsible sheath includes a coil member operable to change the collapsible sheath between the collapsed position and the expanded position.

24. A method of accessing a tissue puncture, comprising:
providing a collapsible sheath and a dilator;
advancing the dilator through the collapsible sheath until a distal end of the dilator extends distal of the collapsible sheath and a length of the collapsible sheath surrounds a portion of the dilator having a reduced diameter relative to the distal end of the dilator;
orienting the collapsible sheath into a collapsed position around the dilator, wherein the distal end of the dilator has an outer dilator diameter equal to an outer collapsible sheath diameter in the collapsed position;
advancing the collapsible sheath and dilator through the tissue puncture with the collapsible sheath in the collapsed position;
orienting the collapsible sheath into an expanded position to dilate the tissue puncture, wherein orienting the collapsible sheath into an expanded position includes rotating one end of the collapsible sheath relative to an opposite end of the collapsible sheath.

* * * * *